US006692196B1

United States Patent
Simm et al.

(10) Patent No.: US 6,692,196 B1
(45) Date of Patent: Feb. 17, 2004

(54) APPARATUS FOR MANUFACTURING HYGIENIC ARTICLES

(75) Inventors: Rolf Simm, Erfstadt (DE); Robert George Cox, Cincinnati, OH (US); Nicholas Minde, Cologne (DE); Timothy Alan Burkett, Houston, TX (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/913,446
(22) PCT Filed: Feb. 19, 1999
(86) PCT No.: PCT/US99/03597
§ 371 (c)(1),
(2), (4) Date: Jan. 31, 2002
(87) PCT Pub. No.: WO00/48543
PCT Pub. Date: Aug. 24, 2000

(51) Int. Cl.⁷ .............................................. B65G 53/28
(52) U.S. Cl. .................... 406/88; 406/106; 198/465.2; 198/619
(58) Field of Search ................ 198/619, 465.2, 198/106, 86, 88; 406/89; 414/676, 25; 104/155

(56) References Cited

U.S. PATENT DOCUMENTS 3,882,791 A  *  5/1975 Youngscap ............... 104/154
4,781,369 A     11/1988 Mathias
4,825,111 A  *  4/1989 Hommes et al. ............ 104/290
5,086,904 A  *  2/1992 Yasutake ................ 198/346.1
5,130,583 A     7/1992 Andoh
5,722,326 A     3/1998 Post
5,906,262 A  *  5/1999 Miki ..................... 198/341.02
6,223,886 B1 *  5/2001 Bonora et al. ........... 198/465.2

FOREIGN PATENT DOCUMENTS

EP          0 589 859 A1      3/1994
EP          0 689 778 A1      1/1996

* cited by examiner

Primary Examiner—Joseph A. Dillon
(74) Attorney, Agent, or Firm—Kevin C. Johnson; Michael S. Kolodesh

(57) ABSTRACT

An apparatus for manufacturing a series of discrete hygienic articles. The apparatus includes a supply means, at least one manipulation means, a reception means spatially separated from the supply means, a manufacturing path segment extending from the supply means to the manipulation means and continuing to the reception means and a transportation system. The transportation system includes a plurality of independent transportation means for transportation of at least one discrete hygienic article along the manufacturing path segment and a guide means to guide all of the transportation means.

6 Claims, 1 Drawing Sheet

APPARATUS FOR MANUFACTURING HYGIENIC ARTICLES

FIELD OF THE INVENTION

The present invention relates to an apparatus for the manufacture of a series of discrete hygienic articles.

BACKGROUND

Hygienic articles such as absorbent pads, diapers, training pants, adult incontinence devices, sanitary napkins, bed pads, wound dressings and the like are well known in the art. These articles, in particular the disposable hygienic articles, have become a mass market. Hence, these articles have to be manufactured at a high speed and at a low cost.

Generally, such hygienic articles are manufactured by providing a continuous base material such as for example the back sheet or the top sheet, joining other elements of the article to the base material at regular intervals, and finally cutting the continuous web of articles into discrete articles. Such a process and a suitable apparatus are disclosed for example in EP-A-589859.

Whilst being used widely within the industry, these apparatus have inherent restrictions such as a constant speed of the articles along the manufacturing path and a constant orientation of the articles relative to each other along the manufacturing path. Such restrictions imply design limitations which are potentially impeding overall article performance.

SUMMARY OF THE INVENTION

The present invention provides an apparatus for manufacturing a series of discrete hygienic articles. The apparatus comprises a supply means, at least one manipulation means, a reception means spatially separated from the supply means, a manufacturing path segment extending from the supply means to the manipulation means and continuing to the reception means, and a transportation system. The transportation system comprises a plurality of independent transportation means for transportation of at least one discrete hygienic article, at least one discrete precursor of a hygienic article, or at least one discrete element of a hygienic article from the supply means to the manipulation means and subsequently to the reception means and a guide means to guide all of the transportation means.

The apparatus of the present invention provides improved versatility in the automated manufacture of discrete hygienic articles in that it allows, for example, independently programmable article speed variation along the manufacturing path, change of orientation of the article relative to the manufacturing path, increased production layout flexibility, easy adaptation of the manufacturing process, and increased independence of processes.

DETAILED DESCRIPTION OF THE INVENTION

Figure 1:
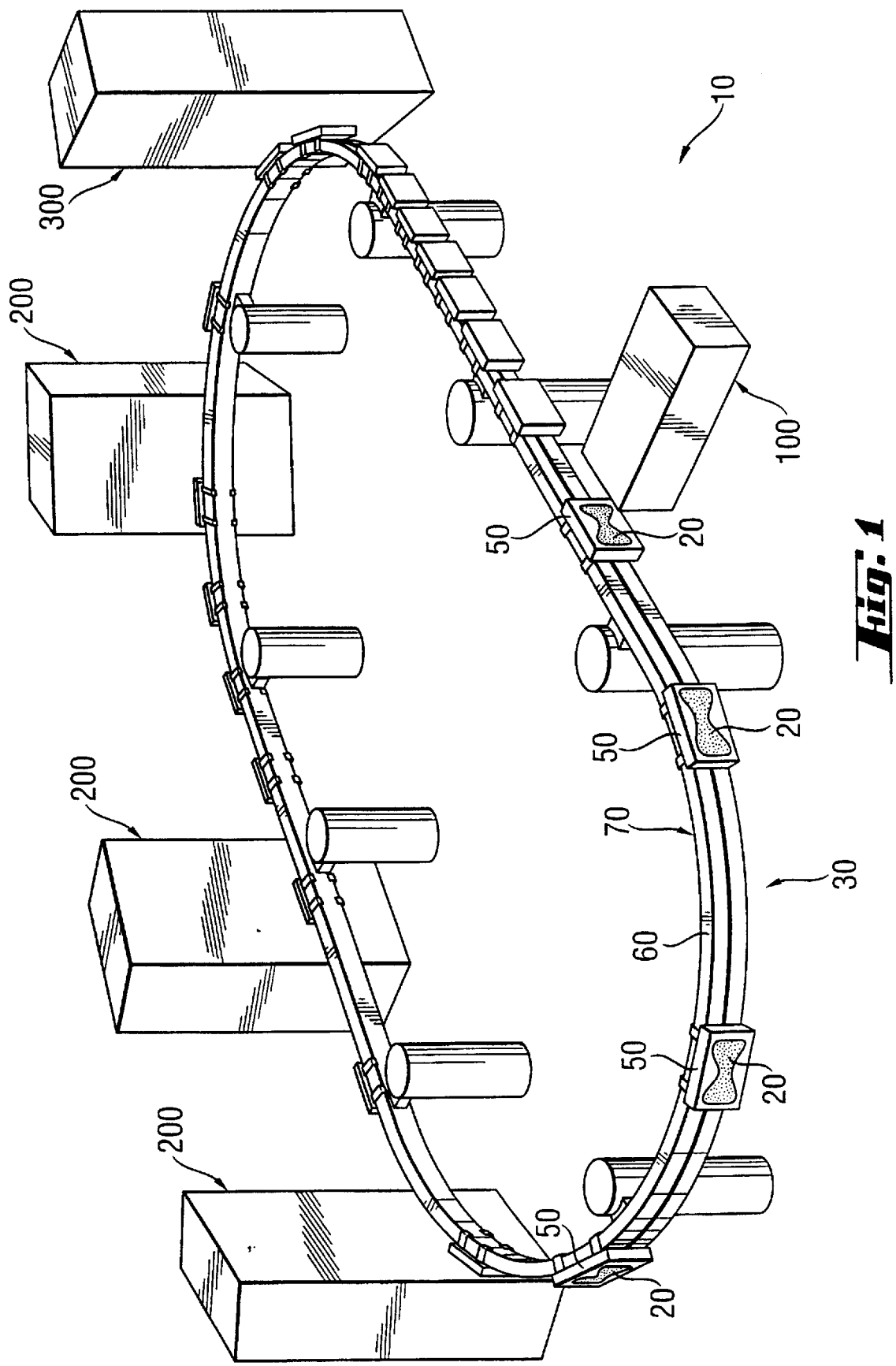
FIG. 1 shows a schematic drawing of one embodiment of the apparatus for manufacturing a series of discrete hygienic articles according to the present invention.

The present invention provides an apparatus for manufacturing a series of discrete hygienic articles. Preferably, the apparatus can manufacture hygienic articles in a continuous process at an output rate of at least 10 articles per minute, more preferably more than 20 articles per minute, even more preferably more than 50 articles per, even more preferably more than 100 articles per minute, most preferably more than 300 articles per minute.

The term "hygienic article" as used herein refers to articles which are intended to be used in contact with or in close proximity to the skin of the user. Hygienic articles include absorbent articles such as absorbent pads, diapers, training pants, adult incontinence devices, sanitary napkins, bed pads, and the like. In addition, hygienic articles comprise articles of low or zero absorbency such as wound dressings, clothing (in particular underwear) and the like.

Hygienic articles of the present invention may be intended for multiple use or they may be disposable. The term "disposable" is used herein to describe hygienic articles which are not intended to be laundered or otherwise restored or reused as a hygienic article after a single use.

The term "element" of an article as used herein refers to any part of the article that is already or intended to be joined to the rest of the article.

The term "precursor" of an article refers to that partially assembled precursor of an article that comprises that element of the article which has been supplied to the process first.

In the following, the present invention is described by means of several particular though not limiting embodiments. The present invention is intended to encompass also those embodiments in which features of several of the described embodiments have been combined as appropriate.

FIG. 1 shows a schematic drawing of one embodiment of the apparatus for manufacturing a series of discrete hygienic articles according to the present invention. The apparatus 10 comprises a supply means 100, at least one manipulation means 200, a reception means 300 spatially separated from the supply means 100, and a manufacturing path segment extending from the supply means 100 to the manipulation means 200 and continuing to the reception means 300. At the supply means 100, the transportation means 50 receives a hygienic article 20, a precursor 20 of a hygienic article, or an element 20 of a hygienic article. The supply means of the present invention may supply discrete hygienic articles, discrete precursors or discrete elements or it may provide a web of articles, precursors, or elements which is cut into discrete pieces shortly after supply to the transportation means. The transportation means then transports the received discrete article, precursor, or element to the manipulation means. Subsequently, the transportation means further transports the discrete article, precursor, or element to the reception means 300 where it is released from the transportation means 50 and received by the reception means 300. After the reception, the articles, precursors, or elements remain discrete for the remainder of the manufacturing process of the discrete hygienic articles.

The term "supply means" as used herein refers to a device that is capable of supplying a discrete hygienic article, a discrete precursor, or a discrete element to a transportation means. The term "supply means" also refers to devices that supplies a continuous web of articles, precursors, or elements to the transportation means and cuts the web into discrete pieces shortly after supply to the transportation means.

The term "manipulation means" refers to any part of an apparatus for the manufacture of articles that performs an action on a hygienic article, a precursor of the article, or any element of the article. Such actions include but are not limited to, adding or removing of elements, change of physical or chemical state such as cutting, folding, heating, compressing and the like.

The term "reception means" as used herein refers to a device that is capable of receiving a hygienic article, a precursor of the article, or any element of the article from a transportation means. The reception means may be positioned at the end of the manufacturing path of the hygienic articles or the reception means may transport to the remaining segment of the manufacturing path.

The term "manufacturing path" as used herein refers to the path of the articles or its precursors through the apparatus from the supply of the precursor of the hygienic article to the point at which the finished articles arrive at the end of the manufacturing process.

The term "manufacturing path segment" as used herein refers to a segment of the manufacturing path between a first manipulation means and a second manipulation means of the apparatus. Further manipulation means may be arranged along the manufacturing path segment and intermediate the first manipulation means and the second manipulation means. In this context, the first manipulation means can be the supply means and the second manipulation means can be the reception means. Typically, the first and second manipulation means are spatially separated from each other such that the article or its precursor needs to be transported from the first to the second manipulation means.

Optionally, further manipulation means 200 may be arranged between the supply means and the reception means such that they can perform actions on the article, precursor, or element 20 while it is carried by the transportation means 50. Examples of such manipulation means are well known to the skilled person and described, for example, in EP-A-589859.

The apparatus 10 of the present invention comprises a transportation system 30 which includes a plurality of independent transportation means 50 each of them designed to transport at least one discrete hygienic article 20, at least one discrete precursor 20 of a hygienic article, or at least one discrete element 20 of a hygienic article from the supply means 100 to the reception means 300 and a guide means 60 to guide all of the transportation means 50. The transportation system 30 is designed such the at the articles 20, precursors 20, or elements 20 are transported along the manufacturing path from the supply means 100 to the manipulation means 200 and subsequently to the reception means 300.

The term "transportation system" as used herein refers to a device that is capable of transporting articles or their precursors between a first manipulation means and a second manipulation means. In this context, the supply means may be substituted for the first manipulation means and the reception means may be substituted for the second manipulation means.

The term "transportation means" as used herein refers to any device that is capable of transporting at least one discrete article or at least one discrete precursor. Typically, a plurality of transportation means are comprised in a transportation system according to the present invention.

The term "guide means" as used herein refers to any device that is used to guide the plurality of transportation means when they are moving along the manufacturing path from the supply means to the reception means. A guide means may comprise subsystems and additional elements such as support means or drive means.

The term "plurality of independent transportation means" as used herein refers to a plurality of transportation means which are supported by the same guide means and which are individually movable along the guide means at least as far as they do not pass each other.

The transportation system 30 of the apparatus of the present invention is different from prior art transportation systems such as conveyor belts in that it allows the individual transportation of at least one discrete article, its precursor, or an element thereof independent of one another. This is achieved by providing a plurality of independent transportation means 50 and a guide means 60. All individual transportation means can be moved along the manufacturing path independent of each other. The transportation means, however, can not pass each other, unless two manufacturing path segments are arranged in parallel (as described below). They are only guided by the guide means. Therefore, the total length of the manufacturing path segment governed by the guide means has to be longer than the combined length of all transportation means.

Optionally, the apparatus 10 of the present invention may comprise more than one transportation system 30 according to the present invention.

Optionally, manipulation means can be incorporated into the transportation means 50 such that these manipulation means can perform an action on the article, precursor, or element 20 while it is carried by the transportation means 50.

When a transportation means 50 has reached the reception means 300 and has released the article 20, precursor 20, or element 20 (i.e. The end of the manufacturing path segment governed by the transportation system of the present invention), the transportation means either has to be disposed of or it has to be transferred back to the supply means 100 (i.e. The beginning of the manufacturing path segment). In one embodiment of the apparatus 10 of the present invention, the guide means 60 is of the closed loop form, i.e. The guide means 60 is designed such that it not only guides the transportation means from the supply means 100 to the reception means 300, it subsequently guides back the transportation means to the supply means 100.

In one embodiment of the present invention, the apparatus has a first path segment and a second path segment of the manufacturing path segment between the supply means and the reception means wherein the linear velocity of the transportation means on the first path segment is substantially different from the linear velocity of the transportation means on the second path segment. Different steps of the process to be carried out by the manipulation means of the apparatus of the present invention may require different speeds of the article, precursor, or element carried by the transportation means relative to the respective manipulation means. With the apparatus of the present invention, it is possible to accelerate or slow down the transportation means, thus allowing for different linear velocities of the article, precursor, or element along the manufacturing path and relative to one another, whilst all conventional apparatus only provide a constant linear velocity of the continuous web relative to the surroundings along the manufacturing path.

The term "linear velocity" as used herein refers to the tangential velocity of a transportation means at its current position on the manufacturing path.

In one embodiment of the apparatus of the present invention, the distance between two consecutive transportation means on a first path segment of the manufacturing path segment between the supply means and the reception means is substantially different from the distance between two consecutive transportation means on a second path segment. Some manipulation steps during the process to be carried by the apparatus of the present invention may require that the transportation means immediately follow each other, for example when a continuous web is laid down on the article precursors carried by the transportation means and then cut into discrete pieces. Other steps may require a certain distance between two consecutive precursors carried by the transportation means, for example when a web material is to be folded around the transversely extending edges of the precursor. The apparatus of the present invention provides the flexibility to change the distance between two consecutively manufactured articles, precursors, or elements along the manufacturing path during manufacture.

In one embodiment of the apparatus of the present invention, a first path segment and a second path segment of the manufacturing path segment between the supply means and the reception means are arranged in parallel. The term "arranged in parallel" as used herein refers to an arrangement of a first path segment and a second path segment such that a transportation means can move exclusively either on the first path segment or the second path segment. In one embodiment, the main manufacturing path forks into two alternative path segments. In another embodiment, the parallel path segments are combined into a single main manufacturing path. Yet another embodiment combines the aforementioned forking into and recombination of parallel path segments. Parallel arrangement of path segments allows to combine manufacturing steps which are carried out at different throughput rates without compromising the throughput rate of the fastest manufacturing step. Parallel arrangement can be used to implement process redundancy. Parallel arrangement also allows that transportation means pass each other.

In one embodiment of the apparatus of the present invention, the orientation of a hygienic article, its precursor or an element of the article relative to a first manufacturing path segment is substantially different from the orientation of article, precursor, or element relative to a second manufacturing path segment. On an apparatus such as well known in the art, the orientation of the single article or precursors was fixed relative to the immediately adjacent articles or precursors since all articles or precursors constituted one continuous web. Hence, the rotation of the web around the manufacturing path axis is possible, the rotation of the individual articles or precursors around an axis perpendicular to the manufacturing path was impossible. Due to the physical independence of the individual articles, precursors, or elements and their respective transportation means, any orientation of the individual articles, precursors, or elements can readily be achieved during manufacture. For example, a rotation device could be integrated into the transportation means such that the individual articles, precursors, or elements can be reoriented according to the process requirement. In yet another embodiment of the apparatus, the transportation means itself can be reoriented relative the manufacturing during manufacture path according to process requirements. With the apparatus of the present invention, a rotation of the article, precursor, or element around any axis (parallel or perpendicular to the manufacturing path) can be achieved.

In one embodiment of the transportation means of the present invention, the transportation means comprise support means such as wheels, rails, or the like which support the transportation means on the guide means and allow movement of the transportation means along the manufacturing path. Preferably, the friction force resisting movement of the transportation along the manufacturing path is low.

In one embodiment of the guide means of the present invention, the guide means comprises a plurality of support means such as air jets supplying an air flow which provides support for the transportation means. In another embodiment of the guide means of the present invention, the transportation means are supported by magnetic levitation such as disclosed for example in U.S. Pat. No. 5,722,326. Air flow support and magnetic levitation are particularly suitable for the present invention because of the low friction they exhibit.

The transportation means of the present invention may be driven by external drive means or by internal drive means. The term "drive" as used herein refers to any force exerted onto the transportation means in order to increase or decrease its speed or to change its direction of travel.

In one embodiment of the apparatus of the present invention, the guide means comprises an external drive means such as a chain having connection means such as hooks that reliably attach to a transportation means. The connection means may be provided at regular intervals along the chain. At certain positions along the manufacturing path the connection means may attach to a transportation means thereby moving the transportation means along the path releasing the transportation means at other certain points. In another alternative embodiment of the guide means of the present invention, the guide means comprises external drive means at certain points of the manufacturing path. These external drive means are capable of transferring a certain impulse to or inducing a certain impulse in the transportation means.

In one embodiment of the transportation and guide means of the present invention, the external drive means comprise means to generate electrical and/or magnetic fields which control position, velocity and acceleration of the transportation means. One example for an external drive means suitable for the present invention is a linear motor such as the apparatus described in U.S. Pat. No. 5,130,583. This technology enables high speeds, high accelerations and very high accuracy of the transportation means because of the fast adjustability electrical and magnetic fields.

In another alternative embodiments, the transportation means are driven by means of an air flow. Such an air flow may be directed towards the transportation means, i.e. Pushing the transportation means. Attentively, the transportation means may be driven by applying vacuum, i.e. By pulling the transportation means.

In another alternative embodiment of the present invention, the transportation means comprise a motor which drives transportation means.

In another alternative embodiment of the present invention, a plurality of drive means may be utilized. This allows the drive means to be optimized for transportation requirements over individual segments of the manufacturing path. For example, transportation means can be controlled by fields over stretches of the manufacturing path that require high positioning precision and/or acceleration and by simple mechanical means such as chains with connecting means where high precision or high acceleration is not required.

What is claimed is:

1. An apparatus (10) for manufacturing a series of discrete hygienic articles (20), said apparatus comprising a supply means having a supply of discrete hygienic articles (100), at least one manipulation means (200)

a reception means (300) spatially separated from said supply means, a manufacturing path segment (70) extending from said supply means to said at least one manipulation means and continuing to said reception means and a transportation system (30) characterized in that said transportation system comprises a plurality of independent transportation means (50) transporting at least one of said discrete hygienic articles (20) along said manufacturing path segment and a guide means (60) to guide all of said transportation means.

2. An apparatus (10) for manufacturing hygienic articles (20) according to claim 1 wherein said guide means (60) is of the closed loop form.

3. An apparatus (10) for manufacturing hygienic articles (20) according to claim 1 wherein said guide means (60) supports said transportation means by electric and/or magnetic fields.

4. An apparatus (10) for manufacturing hygienic articles (20) according to claim 1 wherein said guide means (60) drives said transportation means by electric and/or magnetic fields.

5. An apparatus (10) for manufacturing hygienic articles (20) according to claim 1 wherein said guide means (60) supports said transportation means via air flow.

6. An apparatus (10) for manufacturing hygienic articles (20) according to claim 1 wherein said guide means (60) drives said transportation means via air flow.

* * * * *